United States Patent
Wang et al.

(10) Patent No.: US 11,639,926 B2
(45) Date of Patent: May 2, 2023

(54) DETECTION DEVICE, SAMPLE SOLUTION LOADING DEVICE, TEST STRIP LOADING BOARD AND TEST STRIP

(71) Applicant: Institute of Quality Standard and Testing Technology for Agro-Products, CAAS, Beijing (CN)

(72) Inventors: Jing Wang, Beijing (CN); Zhen Cao, Beijing (CN); Hui Li, Beijing (CN)

(73) Assignee: Institute of Quality Standard and Testing Technology for Agro-Products, CAAS, Beijing (CN)

( * ) Notice: Subject to any disclaimer, the term of this patent is extended or adjusted under 35 U.S.C. 154(b) by 0 days.

(21) Appl. No.: 17/744,555

(22) Filed: May 13, 2022

(65) Prior Publication Data

US 2022/0283156 A1    Sep. 8, 2022

Related U.S. Application Data

(63) Continuation of application No. PCT/CN2020/123256, filed on Oct. 23, 2020.

(30) Foreign Application Priority Data

Nov. 15, 2019    (CN) .......................... 201921971969.8
Nov. 15, 2019    (CN) .......................... 201921977474.6

(51) Int. Cl.
*G01N 33/53*    (2006.01)
*G01N 33/543*    (2006.01)
(Continued)

(52) U.S. Cl.
CPC ... *G01N 33/5302* (2013.01); *G01N 33/54388* (2021.08); *G01N 33/54389* (2021.08); *G01N 35/10* (2013.01); *G01N 2035/00792* (2013.01)

(58) Field of Classification Search
CPC ......... G01N 33/5302; G01N 33/54387; G01N 33/54388; G01N 33/54389; G01N 35/10;
(Continued)

(56) References Cited

U.S. PATENT DOCUMENTS

| 5,981,298 A | * | 11/1999 | Chudzik | G01N 33/558 436/805 |
| 2010/0120173 A1 | * | 5/2010 | Zhou | B01L 3/5025 422/400 |
| 2016/0169882 A1 | | 6/2016 | Snider et al. | |

FOREIGN PATENT DOCUMENTS

| CN | 101261270 | 9/2008 |
| CN | 104964973 | 10/2015 |

(Continued)

*Primary Examiner* — Christopher L Chin
(74) *Attorney, Agent, or Firm* — Morrison & Foerster LLP

(57) ABSTRACT

A detection device, the device comprising a sample liquid bearing device (300), test strips (200), a test strips bearing plate (100) and a signal acquisition positioning assisting device, wherein the sample liquid bearing device (300) comprises two or more samples cells (320) used for containing sample liquid, each of the test strips (200) at least comprises an identity information bearing part (250), a developing part (220) and a capillary part (210), the test strip bearing plate (100) is used for placing the test strips (200) in the same circular ring in a circumferential array radial manner, and the signal acquisition positioning assisting device is arranged on the test strip bearing plate and is used for positioning the test strips.

18 Claims, 6 Drawing Sheets

(51) Int. Cl.
*G01N 35/10* (2006.01)
*G01N 35/00* (2006.01)

(58) Field of Classification Search
CPC ....... G01N 2035/00792; G01N 33/558; G01N 2035/00108; G01N 2035/00118; G01N 35/00732; G01N 2035/00772; G01N 2035/00801; G01N 2035/00821; B01L 2300/0825
USPC ....... 422/400, 401, 402, 403, 420, 421, 425, 422/426, 430; 435/287.7, 287.9, 970, 435/805, 810, 973; 436/169, 170, 514, 436/518, 530, 810
See application file for complete search history.

(56) References Cited

FOREIGN PATENT DOCUMENTS

| | | |
|---|---|---|
| CN | 105388147 | 3/2016 |
| CN | 209894828 | 1/2020 |
| WO | WO 2018/170572 | 9/2018 |
| WO | WO 2021/093555 | 5/2021 |
| WO | WO 2021/093714 | 5/2021 |

\* cited by examiner

DETECTION DEVICE, SAMPLE SOLUTION LOADING DEVICE, TEST STRIP LOADING BOARD AND TEST STRIP

CROSS-REFERENCE TO RELATED APPLICATIONS

This application is a continuing application of International Application No. PCT/CN2020/123256, filed internationally on Oct. 23, 2020, which claims the priority of the Chinese patent application No. 2019219774746, titled "Detection Device, Sample Solution Loading Device, Test Strip Loading Board and Test Strip", filed on Nov. 15, 2019, and claims the priority of the Chinese patent application No. 2019219719698, titled "Detection Device, Sample Solution Loading Device, Test Strip Loading Board and Test Strip", filed on Nov. 15, 2019 to China National Intellectual Property Administration, the disclosures of which are hereby incorporated by reference.

TECHNICAL FIELD

The present disclosure relates to the technical field of immunological detection, and more particularly relates to a detection device, a sample solution loading device, a test strip loading board and a test strip.

BACKGROUND ART

In the prior art, problems such as complicated detection process and poor timeliness exist in the field of target screening during sampling, sample preparation and analysis. For example, when pesticide residues are detected by a chromatographic analyzer, generally 2 days or longer time may be needed for operations of sampling and obtaining the detection results; and professional operators and device support are needed. After the detection results are obtained during detection of the pesticide residues, most of the purchased samples of the same batch generally have appeared on dinner tables of consumers, thereby losing the significance of warning the consumption risk.

An immunochromatographic method is used by most of the existing detection methods for rapidly screening targets. Different target concentrations may cause different chromogenic depths. Since determination of results is easily affected by human subjective factors, the determination of qualitative and quantitative results is not accurate enough.

Therefore, how to provide a detection device that is high in timeliness, simple in operation and low in technical requirements of operators and can screen targets on sample collection sites and accurately collect test results becomes a problem that urgently needs to be solved in the art.

SUMMARY OF THE INVENTION

Embodiments of the present disclosure provide a detection device. By utilizing timeliness of an immunochromatographic method, chromatographic test strips are regularly arranged on a detection device including a signal acquisition and positioning assistance device. Thus, the test strips are arranged radially in a circumferential array, thereby increasing identification accuracy of the test strips, meeting identification accuracy requirements on chromogenic areas of the test strips during data processing, increasing the timeliness of target screening, simplifying operation procedures, lowering technical requirements of operators, achieving the on-site target screening in real time and increasing the accuracy of collecting test results.

The embodiments of the present disclosure provide a detection device, including:

a sample solution loading device including two or more sample cells configured to contain sample solutions;

a test strip that at least includes an identity information loading part, a color-developing part and a capillary part;

a test strip loading board configured to radially place test strips in a circumferential array in the same circular ring area; and a signal acquisition and positioning assistance device arranged on the test strip loading board and positioned outside the arrangement areas of test strips.

In the above implementation process, two or more sample cells of the sample solution loading device may simultaneously contain two or more liquid samples; and when different types of test strips for detecting different targets are put into each sample cell, chromogenic reactions of the multiple targets can be realized. The chromogenic test strips are arranged on the test strip loading board, so that chromogenic results of the multiple targets may be observed and/or subjected to image acquisition. Compared with an arrangement manner of test strips in a non-circumferential array, the test strips in the circumferential array in the same circular ring area are positioned by the signal acquisition and positioning assistance device. Thus, it can be ensured that, when data analysis is conducted on test strip images subjected to image acquisition, corrected image distortion of the test strips (particularly a chromogenic area) tends to be the same. Further, a matching degree between the segmented chromogenic area and an actual chromogenic area is ensured higher in an image processing process of the chromogenic area of the test strips; then the more accurate detection results may be obtained after the matching degree is contrasted with a matched standard numerical value. It can be seen that, the detection device in the present disclosure can increase the identification accuracy of the test strips, meet identification accuracy requirements on chromogenic areas of the test strips during data processing, increase the timeliness of target screening, simplify operation procedures, lower technical requirements of operators, achieving the on-site target screening in real time and increase accuracy of collecting test results.

In addition, according to the combinational design of the signal acquisition and positioning assistance device and the circumferential array, the influence of ambient light on the data acquisition can be decreased in the image acquisition process; the areas in which the test strips are positioned can be accurately segmented and chromaticity in the chromogenic area can be read as long as corresponding information (such as shape, boundary and vertex) of the signal acquisition and positioning assistance device can be identified.

In one possible implementation, the signal acquisition and positioning assistance device includes at least three identifiers, wherein at least one identifier can be distinguished from the rest identifiers.

Totally more than three identifiers are arranged. Plane directions and positions of the acquired images are accurately corrected during the data processing, such as camera offset and inclination of the test strip loading board.

After the test strips in the circumferential array are completely arranged, that the "at least one identifier can be distinguished from the rest identifiers" can achieve an effect of numbering the test strips to determine the order.

In one possible implementation, the circular ring area is divided into a first circular ring area, a second circular ring area and a third circular ring area. When the test strips are arranged in the circumferential array, the second circular ring area is a circular ring area in which the identity information loading part and the color-developing part are positioned; the third circular ring area is a circular ring area in which the color-developing part is positioned; the first circular ring area is a circular ring area of the whole circular ring area beyond the second circular ring area; and the at least three identifiers are arranged in the second circular ring area.

When the test strips are radially arranged in the circumferential array in the same circular ring area on the test strip loading board, the area in which the test strips are positioned is encircled into a circular ring; the circular ring is divided into different areas according to different functional areas of the test strips (such as the identity information loading part, the color-developing part, the capillary part or a water-absorbing part); and the same functional area is positioned in the same circular ring area. A circular ring in which the color-developing part is positioned is defined as the third circular ring area; a circular ring in which the color-developing part and an identity information identification part are positioned is defined as the second circular ring area; and the remaining circular ring area is defined as the first circular ring area.

During data processing, major objects of image recognition are the identity information loading part and the color-developing part. Therefore, the at least three identifiers are arranged in the second circular ring area, so that the accuracy of image recognition can be increased.

In another possible implementation, the identifiers are close to the edge of the test strip loading board.

The identifiers are arranged on the test strip loading board. The identifiers may be far away from the central position as much as possible when arranged on the edge of the test strip loading board, so that angles and positions of pictures can be accurately corrected by the identifiers when the obtained images are recognized.

In one possible implementation, distribution of the at least three identifiers includes circumferential array distribution surrounding the center of the circular ring.

The distribution manner of the identifiers is set to be the same as that of the test strips, so that data processing procedures can be simplified; and the accuracy of image correction is increased.

In one possible implementation, for that the "at least one identifier can be distinguished from the rest identifiers", the identifiers are distinguished by any one or at least two of color, shape or pattern.

Elements that can distinguish the identifiers can be applied to the identifiers. The pattern may be arrangement of positioned points, a wavy pattern and the like.

Optionally, the identifiers are distinguished by the color. The color includes any one or a combination of at least two of blue, green and yellow.

For colored light of the same wavelength, eyes or imaging equipment generally may feel that the colored light changes when light intensity changes; and only three colors such as yellow, green and blue are constant. The accuracy of image data processing can be increased by selecting any one or at least two of the colors such as blue, green and yellow to distinguish the identifiers.

Optionally, the shape of the identifiers includes any one or a combination of at least two of rectangle, triangle and pentagram.

Boundaries of the rectangle, triangle and pentagram are straight lines and have clear vertexes. Thus, identification accuracy of the edges of the identifiers is easily increased during data processing, thereby accurately segmenting the color-developing areas.

In one possible implementation, the size of a side length of each identifier is more than or equal to 2 mm.

Optionally, the area of each of the identifiers accounts for 0.4-5% of the area of an upper surface of the test strip loading board.

Under existing camera pixels (such as about 12 million pixels), the identification accuracy of the image on the identifiers can be well met during data processing through the identifier size of more than 2 mm. If the identifier size is too small (less than 2 mm), data is wrongly read during image recognition. Besides, if the area of each of the identifiers accounts for 0.4-5% of the area of the upper surface of the test strip loading board, the influence of the colors of the identifiers on chromaticity of the acquired images can be decreased as much as possible.

In one possible implementation, connecting lines of geometric centers of the identifiers are encircled into a square area. The center of the square area coincides with the center of the circular ring area.

In another possible implementation, the identifiers are square identifiers; connecting lines of the centers of the square identifiers are encircled into a square area; and sides of the square identifiers are parallel to the sides of the square area.

In the above implementation, the square area encircled by the identifiers has the same side and angle; an algorithm is simpler during data processing; and particularly, when the identifiers are squares, the algorithm is simpler in operations of identifying the boundaries of the identifiers and correcting offset and angles of the images.

Optionally, in such an implementation, the identifiers include one blue square identifier and three green square identifiers, or one green square identifier and three blue square identifiers.

In one implementation, the upper surface of the test strip loading board is a regular polygon; and when the test strips are arranged in a circumferential array, the test strips or extended areas of length directions of the test strips may cover endpoints of the regular polygon.

Namely, the test strip loading board is a regular polygon; and the test strips are arranged in a connecting line direction of the center of a circle and the vertex. According to such an arrangement manner, the upper surface of the test strip loading board can be utilized to the full extent, thereby decreasing the size of the test strip loading board.

Compared with a circular test strip loading board, the test strip loading board in the present disclosure decreases the area of the upper surface and is more convenient to be held.

Optionally, when the test strips are arranged in the circumferential array, the test strip loading board can at least load the identity information loading part and the color-developing part of the test strips.

Optionally, the vertex, which is the farthest away from the center of the regular polygon, of each identifier on the test strip loading board is positioned on the circumference of a maximum inscribed circle of the regular polygon.

The size of the test strip loading board can be further decreased by only loading the identity information loading part and the color-developing part of the test strips to be used for meeting the requirements of image acquisition. In other words, image acquisition may be not conducted on the capillary part and other parts that have little relation to data processing. However, to well correct the acquired images, the identifiers are arranged on the circumference of the maximum inscribed circle of the test strip loading board, so that the accuracy of image correction can be increased; and the algorithm is simplified.

In one possible implementation, the upper surface of the test strip loading board is a diffuse reflection surface.

Optionally, the upper surface of the test strip loading board is a neutral color surface.

The diffuse reflection surface can decrease light spots caused by reflection of a light source irradiating the surface of the loading board, and decrease the influence on the accuracy of image recognition, while the neutral color surface can decrease the influence of a background color of the loading board on an area needing to be identified, and increase the accuracy of image recognition. According to the limitation of the upper surface of the test strip loading board, interference of a background light source on the upper surface can be decreased during image acquisition, thereby increasing the universality of target screening.

In one possible implementation, when the test strips are arranged in the circumferential array, the upper surface of the test strips is lower than the upper surface of the test strip loading board; and a distance value between the upper surface of the test strips and the upper surface of the loading board is less than $\frac{1}{3}$ of a width value of the test strips (such as $\frac{1}{4}$, $\frac{1}{5}$, $\frac{1}{6}$, $\frac{1}{7}$, $\frac{1}{8}$, $\frac{1}{9}$ and $\frac{1}{10}$); or the upper surface of the color-developing part of the test strips is flush with the upper surface of the test strip loading board; or the upper surface of the test strips is higher than the upper surface of the test strip loading board.

In one possible implementation, when the test strips are arranged in the circumferential array, the upper surface of the color-developing part of the test strips is flush with the upper surface of the test strip loading board; or the upper surface of the test strips is higher than the upper surface of the test strip loading board.

If the position of the test strips is too lower than the upper surface of the test strip loading board (for example, a distance of the upper surface of the test strips lower than the upper surface of the test strip loading board is greater than $\frac{1}{3}$ of the width of the test strips), too much shadow appears in the color-developing part; and after the image recognition, a color error is caused by identification of the color-developing area of the segmented color-developing part, thereby affecting the determination of screening results of the targets.

In one implementation, the test strip loading board includes a board body, and a test strip limiting device arranged on the board body. The test strip limiting device is configured to limit the test strips when the test strips are arranged in the circumferential array in the same circular ring area.

Optionally, the test strip limiting device includes any one or a combination of at least two of a limiting block, a limiting groove, a limiting baffle and a limiting slot.

In a specific implementation, the test strip loading board includes a board body, and test strip loading grooves formed in the board body. The test strip loading grooves are arranged in a circumferential array on the board body surrounding the center of the circular ring area.

Optionally, the length of the test strip loading grooves is more than or equal to the sum of lengths of the identity information loading part and the color-developing part.

Conventionally, the length of the test strip loading grooves is related to the size of the test strip loading board. However, the length of the test strip loading grooves may also be designed alone, such as a manner of enabling the test strips to extend out of the test strip loading board.

Optionally, a depth of the test strip loading grooves is matched with a thickness of test strip.

The matching means that the depth of each of the test strip loading grooves is consistent with the thickness of each test strip, or the difference between the depth and the thickness is maintained in a machining error range.

Optionally, the depth of each of the test strip loading grooves is greater than the thickness of each test strip; and supporting parts are arranged at the bottoms of the test strip loading grooves, used for separating the lower surfaces of the test strips from the bottoms of the test strip loading grooves.

The test strips have been subjected to sample solution chromatography before placed in the test strip loading grooves. If the test strips are tightly attached to the bottoms of the test strip loading grooves, the sample solution may contaminate the test strip loading grooves from the back of the test strip. Therefore, the lower surfaces of the test strips are separated from the bottom of the test strip loading grooves by the supporting parts, thereby avoiding the residual sample solution on the test strips from contaminating the test strip loading grooves.

Optionally, according to the height of the supporting part, the upper surface of the color-developing part of the test strip can be elevated to be flush with the upper surface of the test strip loading board, or the upper surface of the test strip can be elevated to be higher than the upper surface of the test strip loading board.

As mentioned above, such a design can decrease shadow caused by blocking around the test strips during image acquisition. That the upper surface of the color-developing part of the test strip is elevated to be flush with the upper surface of the test strip loading board is to elevate at least the upper surface of the color-developing part of the test strip to be flush with the upper surface of the test strip loading board.

Optionally, the quantity of the supporting parts is at least two.

According to the arrangement of the at least two supporting parts, flatness of the test strips during placement can be increased, thereby avoiding deviation caused by a gravity center problem.

Optionally, a groove width of the test strip loading grooves is 0.1-0.2 mm wider than that of the test strip, thereby ensuring that the test strips can be placed in the grooves and form narrower gaps with the edges of the grooves, increasing the accuracy of image acquisition and decreasing the influence of gap shadow.

Optionally, a shape of the end of a loading area of the identity information loading part of the test strip loading grooves is matched with the shape of the end of the identity information loading part.

Herein, the matching includes matching of the shape and the size. The matching also includes consistency or remaining of the machining error range. Either the limitation of the groove width of the test strip loading grooves or the limitation of the end of the test strip loading grooves is to decrease probability that the gaps produced when the test strips are placed in the test strip loading grooves are wrongly considered as information of the identity information loading part during data processing.

In one implementation, the sample solution loading device and the test strip loading board are arranged independently.

The independent arrangement means that, the sample solution loading device and the test strip loading board can be detached, and can also be installed in a matched manner.

In one implementation, the sample solution loading device includes at least two sample cells that can independently contain the sample solution; and each of the sample cells has the same volume.

The sample solution is independently contained for in order to avoid a condition that color-developing results of adjacent test strips are affected after immobilized reagents on the test strips are dissolved in a process of detecting the sample solution by the test strips. It shall be indicated that, the sample solution in the sample cells may be the same or different. Sample solutions for screening the targets in embodiments of the present disclosure may be the same. However, the to-be-screened targets have differences, such as screening of multiple pesticide residues, fungal toxins and environmental pollutants in tea. The sample solutions for screening the targets in the embodiments of the present disclosure may be different, i.e., in-vitro sample solutions of different sources are screened, such as urine and blood of different people.

In one implementation, the sample cells is provided with a first side wall and a second side wall that are arranged opposite to each other and have a height difference; the first side wall is the one with lower height; and the second side wall is the one with higher height.

The first side wall of each of the sample cells is integrally designed and encircled into a residual sample solution containing cavity; or the detection device further includes a third side wall; and the first wall and the third side wall are integrally designed and encircled into the residual sample solution containing cavity.

In the embodiments of the present disclosure, the sample cells are set as side walls of different heights by a barrel principle; and the amount of the sample solutions in the sample cells is unified, thereby increasing operating accuracy in the test strip chromatography process. The first side walls are integrally designed, or integrally designed by virtue of an additional side wall (the third side wall), and then encircled into the residual sample solution containing cavity, so that ambient pollution is decreased; and excessive sample solutions directly enter the residual sample solution containing cavity. The first side wall is one side wall having the shortest cavity wall of the sample cell.

Optionally, notches configured to fix the test strips are formed in the second side walls.

Optionally, the width of the notches is matched with the width of the test strips.

Optionally, at least the width of the bottom of the first side wall is matched with the width of the test strips.

In the embodiments of the present disclosure, the notches and the design of the sizes of the notches and the width of the bottom of the first side walls are used for avoiding conditions that the sample solution detection process is unstable, the amount of the sample solutions for test strip chromatography is non-unified and the color-developing results are inaccurate due to inclined or dynamic movement of the test strips produced in detection of the sample solutions. Specifically, only part of the test strip below a Max line needs to be immersed into the sample solutions; a longer part is overhead; the gravity center easily deviates; and the test strips can be fixed by the notches, thereby decreasing tipping of the test strips. The notches are matched with the widths of the test strips, so that the test strips can be further fixed, thereby avoiding swaying. However, fixation of the test strips depending on the notches only belongs to single-point fixation, and the fixing effect needs to be increased. Therefore, the width of the bottom of the first side wall is designed to be matched with the width of the test strip, so that two-point fixation can be realized, thereby stably fixing the test strips in the same angle.

In an optional implementation, the sample solution loading device includes sample cells having the same quantity as the test strips. The sample cells are provided with first side walls, and second side walls higher than the first side walls. The sample cells are arranged along the same circumference. The first side walls are encircled into a cylinder; a bottom board is arranged at the bottom of the cylinder so as to form the residual sample solution containing cavity; and the second side walls are encircled into a cylinder so as to form the outer wall of the sample solution loading device.

In the above implementation, the circular arrangement easily realizes the two-point fixation; and the device is small in occupied volume and convenient to carry.

In another implementation, a leakage channel smaller than the width of the capillary part is formed in the bottom of the sample cells; and an outlet of the leakage channel is formed above the capillary part when the test strips are arranged in the circumferential array.

In such an implementation, the test strips are tiled on the test strip loading board; the sample cells are arranged above the capillary part of the test strips; and the sample solutions permeate into the capillary part via the leakage channel so as to conduct sample solution chromatography on the test strips. According to such an implementation, a step of inserting the test strips into the sample cells is avoided; and a problem that the test strips cannot be fixed is solved.

In one implementation, the sample solution loading device is in detachable connection with the test strip loading board.

Optionally, the detachable connection includes any one or a combination of at least two of buckled connection, concave-convex matched connection and threaded connection.

In the embodiments of the present disclosure, when the test strips are inserted into the sample cells for performing sample solution chromatography, the gravity center moves outside; and the test strips is easily out of balance, thereby tipping the sample cells and leaking the sample solutions. However, the detachable connection includes detachable connecting components; and the sample solution loading device and the test strip loading board can be connected when the connecting components are connected, thereby increasing stability of the sample solution loading device and avoiding the sample cells from tipping.

As an optional implementation, an embedded groove is formed in the test strip loading board; and a bulged part matched with the embedded groove is arranged at the bottom of the sample solution loading device. The concave-convex matched connection manner is simple, easy and convenient to operate. Thus, the probability that the sample solutions leak due to action amplitudes during detachment or connection is low. In one implementation, the test strip further includes a water-absorbing part.

The design of the test strips generally includes the capillary part and the color-developing part, while for increasing the detection chromatography amount of the sample solutions, the water-absorbing part is arranged at one end of the color-developing part away from the capillary part, and configured to increase the detection rate of the sample solutions.

Optionally, the identity information loading part covers the capillary part and/or the water-absorbing part.

The identity information loading part is loaded with information including but not limited to varieties, brands and production batch numbers of the test strips, and is mainly used for selecting corresponding standard databases during data processing. Therefore, the identity information loading part may be understood as information that can be identified, such as QR codes, bar codes and numbers. The identity information part can be loaded on a single-layer film, while the single-layer film loaded with the identity information may be attached to any part of the test strip except for the color-developing area, typically including the capillary part and/or the water-absorbing part.

Optionally, the test strip includes the capillary part, the color-developing part and the identity information loading part. A distance between a T line (test line) and a C line (control line) in the color-developing part is 5-8 mm; and the width of the T line and C line in the color-developing part is 0.5-1 mm.

According to the suitable size and distance of the T line and C line, the identification accuracy of the T line and C line can be increased during data processing; and the influence of the ambient light is decreased.

In one implementation, the signal acquisition and positioning assistance device is used for positioning each of the test strips during signal acquisition.

It shall be indicated that, the signal acquisition and positioning assistance device in the embodiments of the present disclosure may have the following effects: correcting the acquired images by the signal acquisition and positioning assistance device according to standard data (including data such as boundary, size and position) of the signal acquisition and positioning assistance device built in a data processing center, thereby correcting the angles and positions of the acquired images; segmenting an identity recognition area according to a preset area of an identity recognition region built in the data processing center, and reading identity information; and segmenting the color-developing area according to a preset position of the color-developing area built in the data processing center, identifying a chromatic value of the color-developing area, acquiring chromatic ratios of the T line and C line, and matching chromatic ratios of the standard databases, thereby obtaining qualitative or quantitative screening results of the targets.

Optionally, the signal acquisition and positioning assistance device is used for positioning the position area of the identity information loading part and the position area of the color-developing part of each test strip during signal acquisition.

As an optional implementation, the detection device includes:

a sample solution loading device, wherein the sample solution loading device includes sample cells having the same quantity as the test strips; the sample cells are provided with first side walls, and second side walls higher than the first side walls; the sample cells are arranged along the same circumference; the first side walls are encircled into a cylinder; a bottom board is arranged at the bottom of the cylinder so as to form the residual sample solution containing cavity; and the second side walls are encircled into a cylinder so as to form the outer wall of the sample solution loading device;

a test strip, including a capillary part, a color-developing part and a water-absorbing part arranged in sequence, wherein an identity information loading part covers the upper surface of the water-absorbing part;

a test strip loading board, wherein the upper surface of the test strip loading board is a white diffuse reflection surface and is in the shape of a regular polygon; the test strip loading board includes a board body, and test strip loading grooves formed in the board body; according to the test strip loading grooves, the upper surface of the color-developing part of the test strip is flush with the upper surface of the test strip loading board; and the test strip loading grooves are arranged on the board body in a circumferential array surrounding the center of a circular ring area;

a signal acquisition and positioning assistance device, including one blue square identifier and three green square identifiers arranged on the test strip loading board, wherein connecting lines of geometric centers of the square identifiers are encircled into a square area; the center of the square area coincides with the center of the circular ring area; at least two sides of the square identifiers are parallel to sides of the square area; and a vertex, which is the farthest away from the center of the circle, of the square identifier is positioned on the edge of the test strip loading board in the shape of the regular polygon.

In the above optional implementation, according to the depth of the test strip loading grooves, or a placement depth of the test strips matched with the supporting parts, the upper surface of the color-developing part of the test strip can be flush with the test strip loading board, i.e., only one test strip loading groove of which the depth is matched with the thickness of the test strip is designed, or one test strip loading groove with the supporting part is designed. When the test strip is arranged in the test strip loading groove, the upper surface of the color-developing part of the test strip can be elevated to be flush with the upper surface of the test strip loading board by the supporting part.

The embodiments of the present disclosure further provide a sample solution loading device. Due to the arrangement of multiple sample cells having the same volume, the volume of the sample cells is standardized by utilizing the barrel principle; the same sample amount is provided for sample solution chromatography of the test strips; and the sample solution chromatography of the test strips is standardized, thereby decreasing color-developing differences of the test strips caused by different sample solution amounts.

The embodiments of the present disclosure provide a sample solution loading device, including at least two sample cells that can independently contain sample solutions; and each of the sample cells has the same volume.

Each of the sample cells is provided with a first side wall and a second side wall that are arranged opposite to each other and have a height difference; the first side wall has is the one with a lower height; and the second side wall is the one with a higher height.

The first side wall of each of the sample cells is integrally designed and encircled into a residual sample solution containing cavity; or the sample solution loading device includes a third side wall; and the first wall and the third side wall are integrally designed and encircled into the residual sample solution containing cavity.

Since the first side wall is one side wall having the lower height, it can be considered that the first side wall is the side wall having the minimum height in the side walls of the sample cells. According to the barrel principle, the volume of the sample cells depends on the first side wall having the minimum height, thus the sample cells provided with the first side walls and the second side wall of the same height have the same volume; and the distance between the first side wall and the second side wall is the same. When the sample solution chromatography is conducted on the test strips, angles of inclination are the same, thus the sample solution chromatography behavior can be consistent, thereby ensuring the same detection chromatography amount of the sample solution and obtaining more accurate test results.

The sample solution loading device provides the multiple sample cells having the same volume; and the sample solution detection amount can be kept consistent when the sample solution chromatography is conducted on the test strips in the sample cells, i.e., the operation of the test strip for detecting the samples can be standardized by the sample loading device; and color-developing errors causing unreliability of the test results brought by inconsistent sample detection behaviors are decreased.

In one implementation, the notches configured to fix the test strips are formed in the second side walls.

Optionally, the width of the notches is matched with the width of the test strips.

Optionally, at least the width of the bottom of the first side wall is matched with the width of the test strips.

During sample solution detection, the sample solution immerses the MAX line at most. If the sample solution goes beyond the MAX line, an experimental error may be caused. Therefore, when the sample solution chromatography is conducted on the test strips, the angle of inclination is larger; the gravity center moves outside; and due to the design of the notches, the test strips may be approximately fixed at an approximate angle. However, after the sizes of the notches are designed (the width of the notches is matched with the width of the test strips), the test strip can be firmly fixed, thereby decreasing sway of the test strips from side to side. Further, the width at the bottom of the first side wall is designed to be matched with the width of the bottom of the test strips, so that two-point fixation of the test strips can be realized; and the test strips are firmly fixed at the same angle, thereby achieving operating consistency of the sample solution chromatography behavior of the test strips.

In one implementation, the sample solution loading device is provided with the sample cells having the same quantity as the test strips. The sample cells is provided with the first side wall, and the second side wall higher than the first side wall. The sample cells are arranged along the same circumference; the first side walls are encircled into a cylinder; a bottom board is arranged at the bottom of the cylinder so as to form the residual sample solution containing cavity; and the second side walls are encircled into a cylinder so as to form the outer wall of the sample solution loading device.

According to the cylindrical arrangement, the arrangement area can be decreased; and the device is convenient to carry. Meanwhile, when the sample solution loading device serves as a reusable product or a disposable product, both carrying cost and manufacturing cost will be greatly decreased.

In another specific implementation, a leakage channel is formed in the bottom of the sample cells.

In such an implementation, the test strips do not need to be specially taken out to be placed in the sample cells for detecting the sample solutions, and may be directly radially arranged in a circumferential array; and the leakage channel of the sample loading device is aligned at the capillary part of the test strips so as to quantitatively leak the samples, thereby realizing the sample solution chromatography. In addition, according to the arrangement of the sample solution loading device, a step of inserting the test strips into the sample cells can be avoided; and a problem that the test strips cannot be fixed is solved.

In one implementation, the sample solution loading device is provided with connecting components in detachable connection. The connecting components include any one or a combination of at least two of buckles in buckled connection, grooves in concave-convex matched connection, bulges in concave-convex matched connection, internal threads in threaded connection, external threads in threaded connection, south poles in magnetic connection and north poles in magnetic connection.

The sample solution loading device is designed into a manner that the device can be in detachable connection with the test strip loading board. According to different detachable connection manners, the detachable connecting component of the sample solution loading device is any one of components that can be known by those skilled in the art and can be in detachable connection.

The embodiments of the present disclosure further provide a test strip loading board. According to the test strip loading board, the test strips can be radially arranged in a circumferential array manner. Meanwhile, the acquired images can be corrected to be matched with images built in a data processing system.

The embodiments of the present disclosure further provide a test strip loading board, including:

a board body;

a test strip limiting device that can limit an arrangement area of the test strips, wherein the arrangement area is arranged in a circumferential array in the same circular ring area in a radial shape; and a signal acquisition and positioning assistance device arranged on the upper surface of the board body.

The test strip limiting device is configured to limit the test strips at specific positions. The signal acquisition and positioning assistance device is configured to correct angles and positions of the acquired images, i.e., information of the signal acquisition and positioning assistance device and corresponding information built in the data processing system are matched; and then the corresponding information on the test strips is segmented from the corrected acquired images according to preset segmentation areas, thereby acquiring the corresponding information of the test strips. According to such a design, interference of the ambient light in the image acquisition process can be avoided; and as long as the corresponding information of the signal acquisition and positioning assistance device can be identified, the areas in which the test strips are positioned can be accurately segmented, and the chromaticity of the color-developing area is read.

In one implementation, the upper surface of the board body is a regular polygon.

The board body in the shape of the regular polygon can decrease use of the material of the board body, thus the test strip loading device is lightweight and convenient to carry and grasp; and use difficulty is lowered.

In one implementation, the signal acquisition and positioning assistance device includes at least three identifiers, wherein at least one identifier can be distinguished from the rest identifiers.

The position of the test strip limiting device can be labeled by distinguishing the identifiers. For example, while being close to a certain specific identifier, the test strip limiting device is clockwise recorded as a first limiting device, a second limiting device, a third limiting device and the like.

Optionally, the identifiers are close to the edge of the board body.

The farther the identifiers are away from the center, the higher the correction accuracy of the corrected acquired image is after the identifiers are identified.

Optionally, connecting lines of geometric centers of the identifiers are encircled into a square area.

Optionally, the identifiers are square identifiers; connecting lines of geometric centers of the square identifiers are encircled into a square area; the center of the square area coincides with the center of the regular polygon; and two sides of the square identifiers are parallel to sides of the square area.

Areas encircled by the identifiers and subordinate identifiers are all designed into squares. Thus, the algorithm can be simplified; and the information capacity and processing speed of the data processing center are increased.

Optionally, the identifiers include one blue square identifier and three green square identifiers, or one green square identifier and three blue square identifiers.

The blue and green are colors having stable chromaticity and are slightly affected by brightness of the ambient light, so that accuracy is higher during boundary identification, thereby increasing the correction accuracy of the acquired images.

In one implementation, the test strip limiting device is a test strip loading groove. A length of the test strip loading groove is ½-¾ of the length of the test strip.

The test strip loading groove has a major effect of limiting the test strips at preset positions so as to bring convenience to segmentation of the color-developing area and the identity information loading area during image processing. According to the test strip loading groove having the length of ½-¾ of the length of the test strip, the test strips are limited at the preset positions in a flat state.

Optionally, a depth of the test strip loading groove is greater than the thickness of the test strip; and a supporting part is arranged at the bottom of the test strip loading groove, used for separating the lower surface of the test strip from the bottom of the test strip loading groove when the test strip is limited.

When the test strip is arranged in the test strip loading groove, since the test strip is tightly attached to the bottom of the test strip loading groove, the bottom of the test strip loading groove is easily contaminated by the sample solutions due to a capillary action; and complexity of detection of different sample solutions is increased, or cross contamination of the different sample solutions is caused.

It shall be indicated that, the depth of the test strip loading groove may be the same as the thickness of the test strip. The depth of the test strip loading groove may also be greater than the thickness of the test strip, and then the supporting part needs to be arranged, and the upper surface of the color-developing part of the test strip is elevated to be flush with the upper surface of the board body or higher than the upper surface of the board body. Moreover, the depth of the test strip loading groove may also be smaller than the thickness of the test strip, and then the upper surface of the test strip is higher than the upper surface of the board body.

Optionally, at least two supporting parts are arranged.

According to the at least two supporting parts, the color-developing part of the test strip can be well elevated to be flush with the upper surface of the board body.

Optionally, the edge of the test strip loading groove is matched with the edge of a to-be-limited test strip.

The test strip can be well limited when the edge of the test strip loading groove is matched with the edge of the to-be-limited test strip; and information identification of the identity information loading part is not interfered by gaps.

Optionally, the upper surface of the board body is a white diffuse reflection surface.

The white diffuse reflection surface has very small mirror reflection on the light source and reduces the difficulty of identifying the image acquisition results; and the white board body can decrease interference of the ambient light during image acquisition.

The embodiments of the present disclosure further provide a test strip configured as the above detection device. By limiting the distance and width of the T line and C line of the color-developing part, color-developing data is effectively read during data processing; and the influence of the ambient light on the color-developing data is decreased.

The embodiments of the present disclosure provide a test strip. The test strip includes a capillary part, a color-developing part and an identity information loading part. The color-developing part is provided with a T line and a C line; a distance between the T line and the C line of the color-developing part is 5-8 mm; and a width of each of the T lines and C lines is 0.5-1 mm.

When color-developing information is acquired by the test strip, since pixel units are of gradient ramp after data of the color-developing part is acquired, color-developing areas of the two lines can be effectively separated due to an appropriate distance between the T line and C line. Meanwhile, the chromatic values of the T line and C line can be effectively distinguished from a background color. Enough pixel units can be processed by setting an appropriate width of the T line and C line, thereby acquiring the effective chromatic value.

In one implementation, the test strip further includes a water-absorbing part.

The identity information loading part covers the upper surface of the capillary part and/or the water-absorbing part. The identity information loading part may be of a layered structure, such as a film. Figurative images such as QR codes, bar codes and digital codes that can load the identity information are printed on the layered structure. In the test strip in the embodiments of the present disclosure, the main objects of data acquisition refer to the color-developing area and the identity information loading area. Therefore, except for the color-developing area, any part of the test strip may cover the layered structure; and a larger identity information loading part can load more identity information.

Compared with the prior art, the embodiments of the present disclosure have beneficial effects as follows:

(1) According to the detection device matched with the test strips in the circumferential array in the radial arrangement manner and the signal acquisition and positioning assistance device, the acquired images can be corrected after image acquisition; and accurate corresponding areas of the test strips are segmented, thereby increasing the accuracy of data acquisition and increasing the reliability and accuracy of target screening.

(2) According to the sample solution loading device composed of the sample cells having the same design, consistency of the detection conditions (particularly the amount of sample solution) of the test strips can be increased; and the differences of the detection results caused by different operations of the sample solution chromatography steps are decreased.

(3) According to the test strip loading device matched with the test strip limiting devices in the circumferential array in the radial arrangement manner and the signal acquisition and positioning assistance device, the test strip can be radially arranged in the circumferential array surrounding the center of the circle, so that the acquired images are corrected after image acquisition; the accurate corresponding areas of the test strips are segmented, thereby increasing the accuracy of data acquisition and increasing the reliability and accuracy of target screening.

(4) The test strip configured as a specific detection device is provided with the T line and C line having the specific size and distance, so that the color-developing areas of the two lines can be effectively separated during data processing so as to effectively distinguish the chromatic values from the background color; and moreover, the enough pixel units can be processed by the appropriate width of the T line and C line, thereby acquiring the effective chromatic value.

BRIEF DESCRIPTION OF THE DRAWINGS

To clearly describe technical solutions of embodiments of the present disclosure, drawings needing to be used in the embodiments will be briefly introduced below. It shall be understood that, the drawings below merely illustrate some embodiments of the present disclosure. Therefore, the drawings shall not be considered as a limitation to the scope. Other related drawings may be obtained by those ordinary skilled in the art in accordance with these drawings without making creative labor.

DETAILED DESCRIPTION OF THE INVENTION

Figure 1:
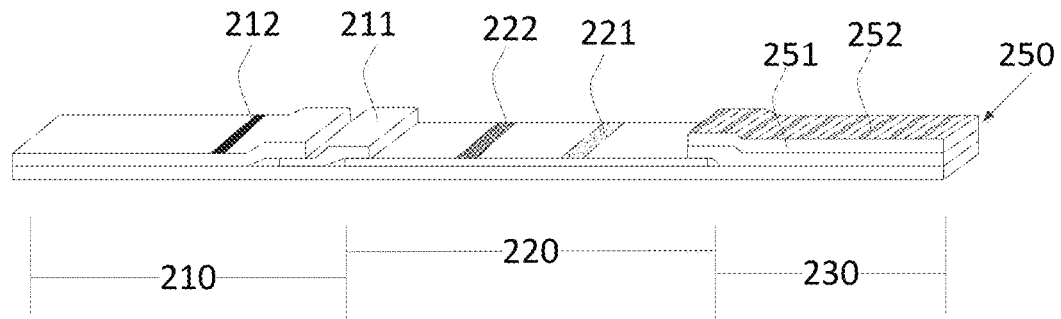
FIG. 1 is a structural schematic diagram of a test strip provided by one specific implementation provided by embodiments of the present disclosure.

For the purpose of making objects, technical schemes and advantages of the present disclosure more clear, clear and complete description will be made to the technical solutions of the present disclosure in conjunction with drawings in the embodiments of the present disclosure. Obviously, the described embodiments are merely a part of the embodiments of the present disclosure and not all the embodiments. Generally, components in the embodiments of the present disclosure that are described and illustrated in the drawings herein may be arranged and designed in various different configurations.

Therefore, the detailed description of the embodiments of the present disclosure provided in the drawings below is not intended to limit the protection scope of the present disclosure, but merely represents selected embodiments of the present disclosure. Based on the embodiments in the present disclosure, all other embodiments obtained by those ordinary skilled in the art without making creative labor shall belong to the protection scope of the present disclosure.

It shall be noted that, similar symbols and letters represent similar terms in the drawings below. Therefore, once a certain term is defined in one drawing, the term shall not be further defined and explained in the followed drawings. In the descriptions of the present disclosure, it shall be indicated that, directional or positional relations indicated by terms such as "upper", "lower", "left", "right", "vertical", "horizontal", "inner" and "outer" are directional or positional relations shown based on the drawings, or are usually placed directional or positional relations of the products in the present application during use. The directional or positional relations are merely intended to describe the present disclosure and simplify the descriptions only, but not indicate or imply that the device or component must have a specific direction and be configured and operated in the specific direction. Therefore, the terms cannot be understood as a limitation to the present disclosure.

In the descriptions of the present disclosure, it shall be indicated that, unless otherwise expressly specified and defined, terms such as "arrange", "mount", "connect" and "connected" shall have generalized understandings. For example, the connection may be fixed connection, or detachable connection or integral connection; the connection may also be mechanical connection or electrical connection; and the connection may be direct connection, or indirect connection through an intermediate medium, or communication inside two components. Specific meanings of the above terms in the present disclosure may be understood by those ordinary skilled in the art according to specific circumstances.

Test Strip:

As shown in FIG. 1, in one specific implementation, a test strip 200*a* is provided. The test strip includes a PVC bottom board (not shown), and a capillary part 210 (having a length of 20 mm) composed of a sample pad (not shown) (made of a glass fiber film) and a colloidal gold bonding pad 211, a color-developing part 220 (made of a nitrocellulose membrane) having a length of 20 mm and a water-absorbing part 230 (made of absorbent paper) having a length of 20 mm that are attached along a chromatography direction of sample solutions in sequence. A starting end of the colloidal gold layer is a MAX line 212; a C line 221 having a width of 0.8 mm and a T line 222 having a width of 0.8 mm are arranged on the color-developing part 220; and a center line distance between the C line 221 and the T line 222 is 7 mm. A layered identity information loading part 250 having a length of 20 mm covers the upper surface of the water-absorbing part 230. The identity information loading part 250 includes a base layer 251 and a bar code 252 that is printed on the upper surface of the base layer 251 and loaded with identity information.

In other specific implementation, the width of the C line 221 may also be set as any of 0.5 mm, 0.6 mm, 0.7 mm, 0.9 mm and 1.0 mm; the width of the T line 22 may also be set as any of 0.5 mm, 0.6 mm, 0.7 mm, 0.9 mm and 1.0 mm; and the distance between the C line 221 and the T line 222 may also be any of 5 mm, 6 mm and 8 mm.

Figure 2:
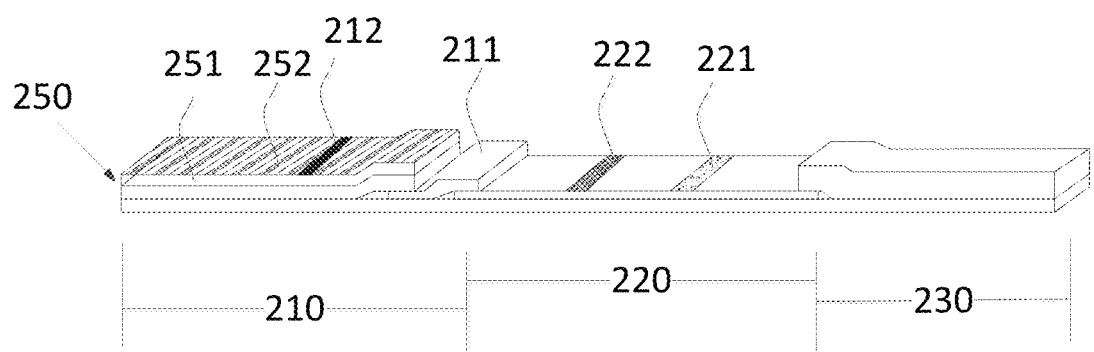
FIG. 2 is a structural schematic diagram of a test strip provided by another specific implementation provided by embodiments of the present disclosure.
Figure 3:
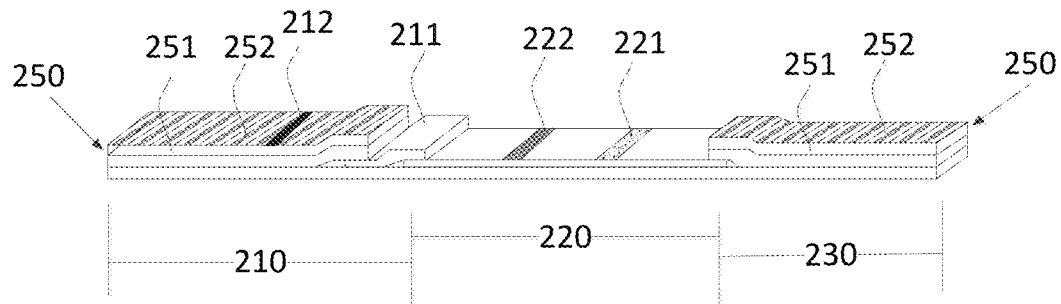
FIG. 3 is a structural schematic diagram of a test strip provided by another specific implementation provided by embodiments of the present disclosure.

In another specific implementation, the layered identity information loading part 250 covers the upper surface of the capillary part 210 (shown as FIG. 2), or the layered identity information loading part 250 simultaneously covers the upper surface of the capillary part 210 and the upper surface of the water-absorbing part 230 (shown as FIG. 3). It shall be indicated that, the water-absorbing part 230 is not an essential structure of the test strip 200. Usually, whether the water-absorbing part 230 is remained can be selected by those skilled in the art according to sample solution conditions and operating requirements.

Figure 4:
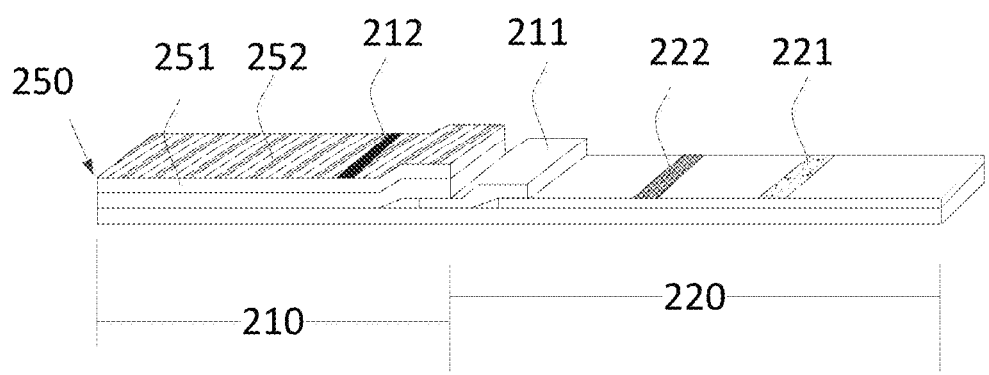
FIG. 4 is a structural schematic diagram of a test strip provided by another specific implementation provided by embodiments of the present disclosure.

As shown in FIG. 4, in another specific implementation, a test strip 200b is provided. The test strip includes a PVC bottom board, and a capillary part 210 (having a length of 20 mm) composed of a sample pad (not shown) (made of a glass fiber film) and a colloidal gold bonding pad 211, and a color-developing part 220 (made of a nitrocellulose membrane) having a length of 20 mm that are attached along a chromatography direction of sample solutions in sequence. The test strip 200 is not provided with a water-absorbing part 230. Meanwhile, an identity information loading part 250 covers the upper surface of the capillary part 210.

In other specific implementation, the identity information loading part 250 may further include a base layer 251 and QR codes, digital codes and shape codes that are printed on the upper surface of the base layer 251 and loaded with identity information.

Figure 5:
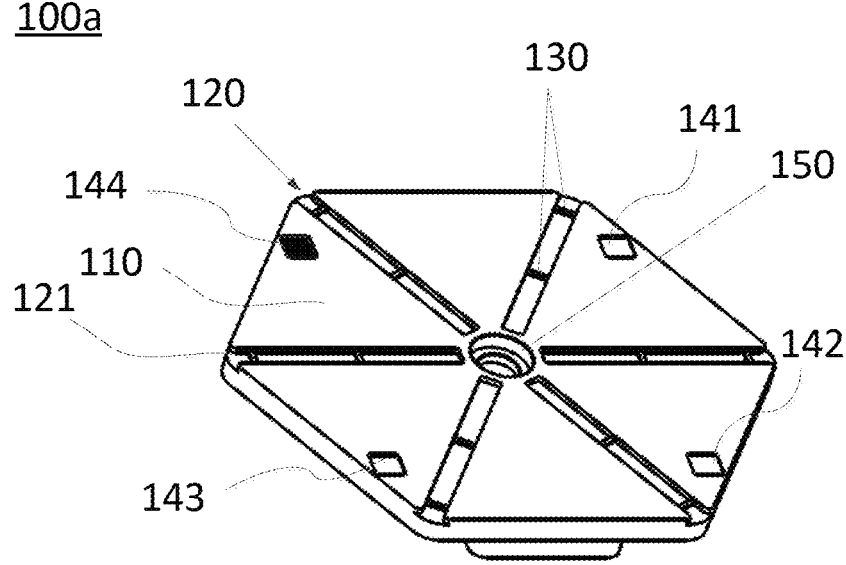
FIG. 5 is a structural schematic diagram of a test strip loading board provided by one specific implementation provided by embodiments of the present disclosure.

In other specific implementation, the size of each of the capillary part 210, the color-developing part 220 and the water suction part 230 may be independently selected from any of 15 mm, 16 mm, 17 mm, 18 mm and 19 mm. Test strip loading board 100:

As shown in FIG. 5, in one specific implementation, a test strip loading board 100a is provided. The test strip loading board includes:

a board body 110, wherein an upper surface of the board body is a regular hexagon; and the upper surface of the board body 110 is a white diffuse reflection surface;

a limiting device 120: six test strip loading grooves 121 are formed in the board body 110; the six test strip loading grooves 121 are arranged in a circumferential array around the center of the regular hexagon (hereinafter referred to as center), and cover the six endpoints of the regular hexagon, and are mutually independent of each other; and the length of the test strip loading grooves 121 is matched with the test strip 200a; and two supporting parts 130 are arranged at the bottoms of the test strip loading grooves 121. A numerical value obtained by subtracting the height of the supporting parts 130 distributed in the test strip loading grooves 121 from the depth of each of the test strip loading grooves 121 is matched with the thickness of the test strip 200a. Thus, the upper surface of the color-developing part 220 of the test strip 200a can be elevated to be flush with the upper surface of the board body 110. The width of each of the test strip loading grooves 121 of the test strip 200a is 0.1-0.2 mm greater than the width of the test strip 200a. Moreover, the shape of the end of each of the test strip loading grooves 121 close to the center is matched with the shape of the test strip 200a.

Three green square first identifiers 141, 142 and 143 and a blue square second identifier 144 are arranged on the upper surface of the board body 110. The four identifiers 141, 142, 143 and 144 are arranged in the circumferential array surrounding the center; connecting lines of geometric centers of the various identifiers are encircled into a square area; the intersection of diagonal lines of the square area coincides with the center of the above regular hexagon; and the farthest point of the identifier away from the center is positioned on the edge of the board body 110. Moreover, a side length of the four identifiers 141, 142, 143 and 144 is 10 mm; and the area of each identifier accounts for 1% of the area of the test strip loading board.

Figure 8:
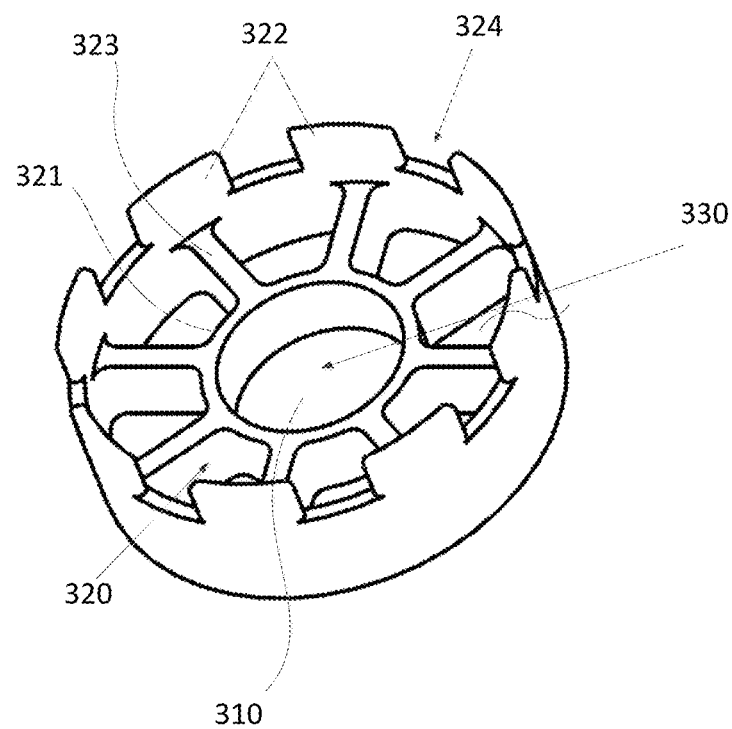
FIG. 8 is a structural schematic diagram of a sample solution loading device provided by one specific implementation provided by embodiments of the present disclosure.

A groove 150 is formed in the center of the board body 110 and is configured to be detachably connected with a sample solution loading device 300 (shown in FIG. 8).

Figure 6:
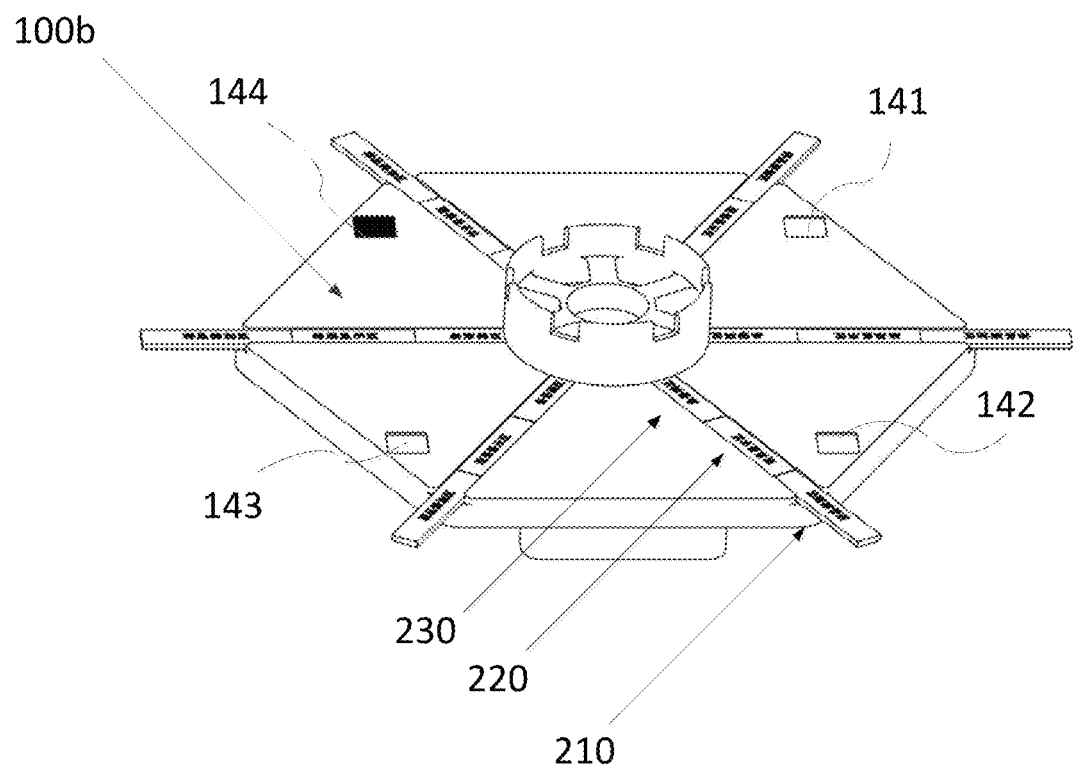
FIG. 6 is a structural schematic diagram of a test strip loading board provided by another specific implementation provided by embodiments of the present disclosure.

As shown in FIG. 6, in another specific implementation, the length of the test strip loading grooves 121 of the test strip loading board 100b is matched with the sum of the length of the water-absorbing part 230 and the color-developing part 220 of the test strip 200a or is slightly greater than the sum of the length of the water-absorbing part 230 and the color-developing part 220 of the test strip 200a.

In such a specific implementation, when the test strip 200a is arranged on the test strip loading board 100b, the water-absorbing part 230 covered by the identity information loading part 250 is close to the center; and the color-developing part 220 and the capillary part 210 are arranged outside the water-absorbing part in sequence. However, most of the capillary part 210 is overhead outside the test strip loading board 10b.

In the test strip loading board 100b, three first blue square identifiers 141, 142 and 143 and a second green square identifier 144 are arranged in the circumferential array surrounding the center; connecting lines of the geometric centers of the identifiers are encircled into a square area; the intersection of the diagonal lines of the square area coincides with the center of the regular hexagon; and the vertexes of the identifiers away from the center are positioned on the edge of the board body 110; and the sides of the square area are parallel to the sides of the identifiers.

In other specific implementation, supporting parts 131 and 132 may not be arranged inside the test strip loading grooves 121. When the supporting parts 131 and 132 are not arranged, the test strip 200a is directly placed at the bottom of the test strip loading grooves 121, thus the test strip loading grooves 121 are easily contaminated by the test strip 200a adsorbed with the sample solutions so as to bring interference to color developing of the next sample solution. However, such a problem can be solved by those skilled in the art by increasing a cleaning step.

Figure 7:
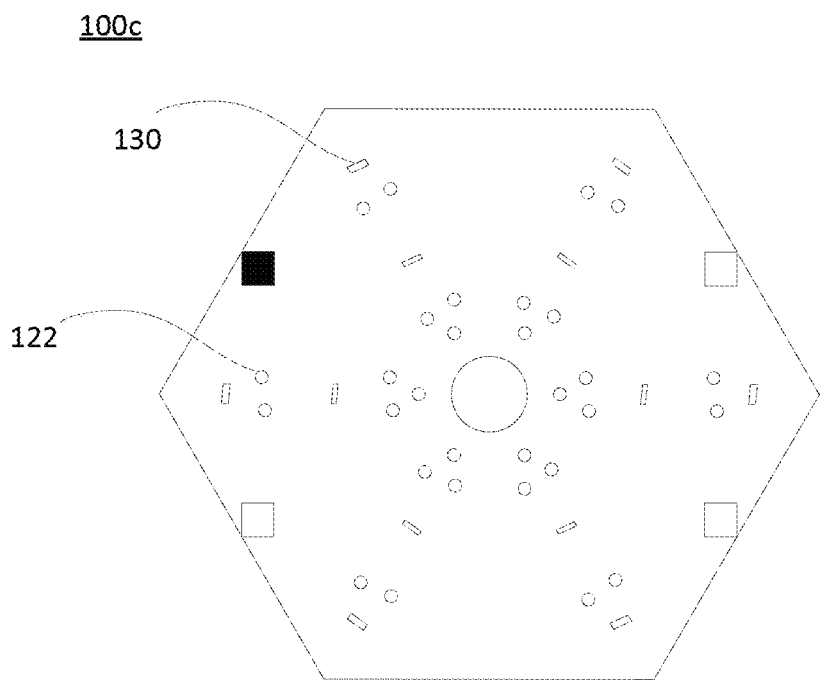
FIG. 7 is a structural schematic diagram of a test strip loading board provided by another specific implementation provided by embodiments of the present disclosure.

As shown in FIGS. 5 and 7, in another specific implementation, a limiting device 120 of a test strip loading board 100c refer to a plurality of limiting cylinders 122 configured to limit positions of the test strip. The size area of the test strip 200a is defined by the limiting cylinders 122.

Certainly, in the test strip loading board 100c, to decrease mutual contamination among the test sample solutions, a supporting part 130 may still be arranged inside the area of the test strip 200a defined by the limiting cylinders 122. The supporting part 130 is configured to separate the test strip 200a from the ground in the limiting area.

In other specific implementation, shapes of the identifiers may be encircled by arc segments and/or linear segments of optional lengths. The identifiers may also be illustratively designed into optional available shapes such as circle, oblong, triangle, pentagram and square.

In other specific implementation, the color of the identifiers may be any one of a combination of yellow and green, a combination of yellow and blue and a combination of yellow, blue and green. Certainly, the color of the identifiers may be selected from red, purple and black. But the colors such as yellow, green and blue stable in hue are slightly affected by the ambient light, and are more suitable for the identifiers.

In other specific implementation, the upper surface of the board body 110 may be in the shape of regular triangle, square, regular pentagon, regular heptagon, regular octagon, regular enneagon and regular decagon.

In other specific implementation, sizes of side lengths of the identifiers may be 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm and the like.

In other specific implementation, the area of each of the identifiers may account for 0.4%, 0.5%, 0.6%, 0.7%, 0.8%, 0.9%, 1.0%, 1.2%, 1.4%, 1.6%, 1.8%, 2.0%, 2.2%, 2.5%, 2.7%, 3.2%, 3.5%, 3.7%, 4.2%, 4.5%, 4.7% and the like of the area of the upper surface of the test strip loading board.

In other specific implementation, the upper surface of the board body 110 may be a gray diffuse reflection surface and a black diffuse reflection surface. The white diffuse reflection surface can acquire more accurate chromaticity read-out value. Neutral colors include black, white and gray.

In other specific implementation, a detachable connecting component or a bulge, a thread, a buckle and a magnetic chuck is arranged in the center of the board body 110. Specifically, when the bulge is arranged in the center of the board body 110, a groove is formed in the bottom of the sample solution loading device; when a groove is formed in the center of the board body 110, a bulge is arranged at the bottom of the sample solution loading device; when an internal thread is arranged in the center of the board body 110, an external thread is arranged at the bottom of the sample solution loading device; when an external thread is arranged in the center of the board body 110, an internal thread is arranged at the bottom of the sample solution loading device; and when a buckle is arranged in the center of the board body 110, a matched buckle is arranged at the bottom of the sample solution loading device. Sample solution loading device 300:

As shown in FIG. 8, in one specific implementation, a sample solution loading device 300a is provided, including: a bottom board 310, wherein a bulged part (not shown) configured to be in detachable connection with the test strip loading board 100 is arranged on the lower surface of the bottom board 310;

six sample cells 320 are arranged on the upper surface of the bottom board 310, wherein each of the sample cells 320 is provided with a first side wall 321 and a second side wall 322 opposite to one another, and two fourth side walls 323 connected with the first side wall 321 and the second side wall 322; the height of the fourth side walls 323 is greater than or equal to the height of the first side wall 321; an outline of the sample cells 320 is fan-shaped; the six sample cells 320 are merged and spliced into a circumference; two adjacent sample cells 320 share the fourth side wall 323; the first side wall 321 is a side wall back to the center of the circumference; the second side wall 322 is a side wall away from the center of the circumference; the first side wall 321 is lower than the second side wall 322; a notch 324 matched with the width of the test strip 200a is formed in the second side wall 322; and the width of a part of the first side wall 321 close to the bottom board 310 is matched with the width of the test strip 200a. The notch 324 is opposite to the part of the first side wall 321 close to the bottom board 310, so that the test strip 200a is prevented from being twisted. The first side wall 321 and the bottom board 310 are encircled into a barrel-shaped residual sample solution containing cavity 330.

Figure 9:
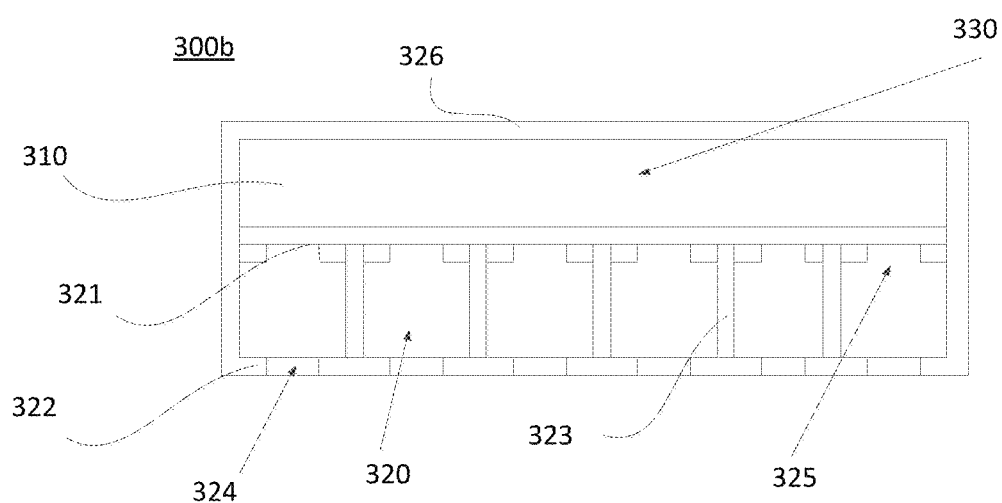
FIG. 9 is a structural schematic diagram of a sample solution loading device provided by another specific implementation provided by embodiments of the present disclosure.

As shown in FIG. 9, in another specific implementation, the sample cells 320 of a sample solution loading device 300b are rectangular and are arranged in parallel in an oblong shape; two adjacent sample cells 320 share the fourth side wall 323; and the first side wall 321, the third side wall 326 and the bottom board 310 are encircled into a rectangular residual sample solution containing cavity 330. A clamping groove 325 is arranged at the place where the first side wall 321 is close to the bottom board 310. The clamping groove 325 is configured to clamp the test strip.

In the above specific implementation, the plurality of sample cells 320 are compactly arranged and share one side wall. Arrangement of the sample cells 320 may be enlarged to a size approximate to the periphery of the test strip loading board 100. The plurality of sample cells 320 are arranged in the shape of a hexagon; and the sample cells 320 are arranged at the endpoints of the hexagonal board body 110.

Figure 10:
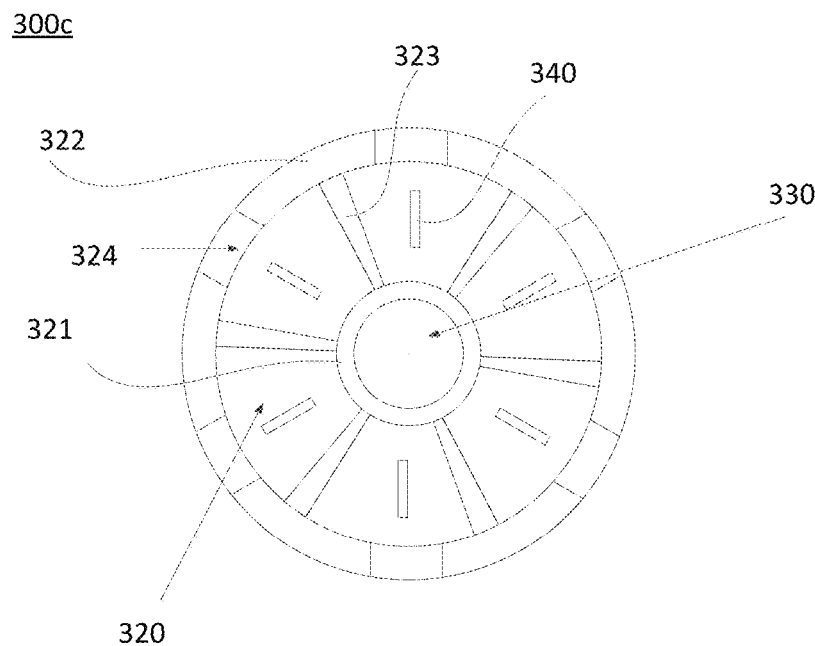
FIG. 10 is a structural schematic diagram of a sample solution loading device provided by another specific implementation provided by embodiments of the present disclosure.

As shown in FIG. 10, in another specific implementation, a leakage channel 340 is formed in a part of the bottom board of the sample solution loading device 300c corresponding to the sample cells 320. The width of the leakage channel 340 is smaller than or equal to the width of the test strip 200a. When the sample solution loading device 300c is in detachable connection with the test strip loading board 100, the leakage channel 340 is aligned at the capillary part 210 of the test strip 200a and configured to direct conduct sample solution chromatography.

By detailed descriptions of the test strips 200a and 200b, the test strip loading devices 100a, 100b and 100c and the sample solution loading devices 300a and 300b, and specific implementation of not shown drawings, technical solutions of the present disclosure are described in detail. However, these specific implementation are merely examples of the technical solutions, rather than forming a limitation to the protection scope of the present disclosure. Replacements of the components in the specific implementation based on the same effect shall belong to the protection scope of the present disclosure.

Next, the detection device will be described on the whole.

Figure 11:
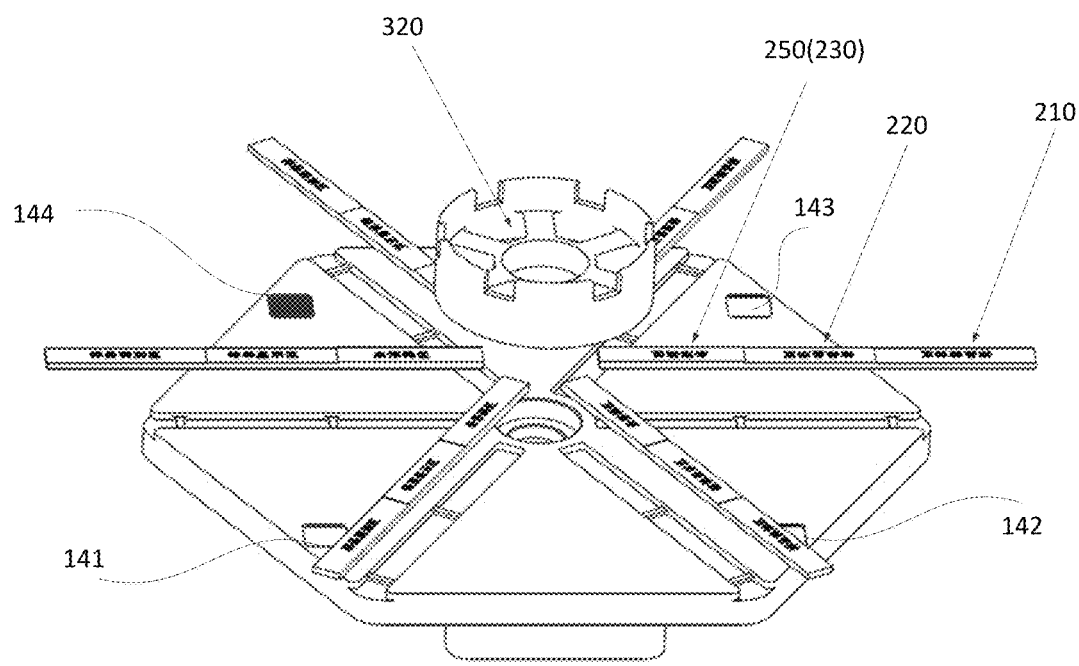
FIG. 11 is a structural schematic diagram of a detection device provided by one specific implementation provided by embodiments of the present disclosure.

As shown in FIG. 11, in a specific implementation, a detection device is provided, including:

a sample solution loading device 300, including two or more sample cells 320 configured to contain sample solutions;

a test strip, at least including an identity information loading part 250 (the lower part covering a water-absorbing part 230), a color-developing part 220 and a capillary part 210;

a test strip loading board 100, configured to enable multiple test strips to be arranged in a circumferential array in the same circular ring area and arranged in a radial shape; and a signal acquisition and positioning assistance device, arranged on the test strip loading board 100.

Specific implementation forms of the sample solution loading device, the test strip and the test strip loading board are described above in detail. The device may be selected by those skilled in the art according to actual requirements. Operating steps and principles are briefly introduced below.

When targets are screened by a target screening detection device provided by the embodiments of the present disclosure, specific operating steps may be illustratively as follows:

(1) Excessive sample solutions are added into the sample cells 320 of the sample solution loading device 300, so that the sample solutions in the sample cells 320 have the same volume. The capillary part 210 of test strips are inserted into the sample cells 320, and test strips are obliquely fixed on cavity walls of the sample cells 320. After sample solution chromatography is conducted by the test strip for a period of time, the test strips are taken out, and then a certain amount of the sample solutions have been subjected to chromatography by test strips. Since the amount of the sample solutions in the sample cells 320 is the same, the inclination angle of the test strips is the same and placement time of the test strips is the same, the amount of chromatography of the sample solutions is basically the same.

(2) After the test strips that complete the sample solution chromatography are taken out, the test strips are radially arranged on the test strip loading board in a circumferential array manner. The capillary part may be inward or outward. The size of the test strip loading board is enough to load the test strips, and part of the test strips may also be overhead. The signal acquisition and positioning assistance device is arranged on the test strip loading board, so that the test strips can be identified by the data processing system, and the angles and positions of the acquired images can be corrected.

(3) After image acquisition, the identity information identification area and the color-developing area are accurately segmented from the acquired images according to the standard segmentation areas built in the data processing center; and the screening results of the targets are read according to identity information of the identity information identification area and the color-developing result of the color-developing area.

It can be seen from the above processes and principles that, the detection device provided by the embodiments of the present disclosure can omit the identification process while acquiring the data of the color-developing part, decrease the interference of the ambient light, and accurately acquire the color-developing information of the color-developing area by depending on the positioning effect of the signal acquisition and positioning assistance device.

For the immunochromatographic assay, conditions that the developed colors are non-uniform, the developed color close to the edge is deep and the developed color in the middle is light often occur during color developing of the color-developing area. Thus, a larger identification error of the color-developing area may be caused when the colors of the color-developing area are directly identified, thereby causing inaccurate detection results. Further, the problem that the accuracy is decreased due to direct identification of the color-developing area can be solved by perform segmentation on the position of each test strip using the built-in programs. However, for the combination of test strips in a non-circumferential array, after the acquired images are corrected, the width and length of each test strip are greatly related to the position of the test strip. For example, for test strips in an oblong array, obvious differences may be caused between sizes of test strips close to a simulation camera and test strips away from the simulation camera (the simulation camera refers to a position of a simulation camera for corrected images) because everything looks small in the distance and big on the contrary, so as to cause an error to the detection process of segmenting the target areas via the built-in programs.

In a word, the circular array of the test strips in the embodiments of the present disclosure can ensure that each test strip has the same distortion after the images of data acquisition of the test strips are corrected, so that the requirement on the positional accuracy is met when the color-developing area is accurately segmented via the built-in programs, thereby accurately segmenting the color-developing area.

Certainly, the above principle is merely a description of the process and principle of the detection device provided by the embodiments of the present disclosure, rather than forming a structural definition of the detection device in the present disclosure, i.e., the detection device in the present disclosure may be configured to adapt to the above process and principle, and may also be configured to adapt to any optional process and principle.

In detail, the sample solution loading device of the detection device provided by the embodiments of the present disclosure is the sample solution loading device 300*a* or 300*b* or any specific implementation not shown in the drawings. The test strip is the test strip 200*a* or 200*b* or any specific implementation not shown in the drawings. The test strip loading board is the test strip loading board 100*a*, 100*b* or 100*c* or any specific implementation not shown in the drawings. Specific implementation of the sample solution loading device, the test strip and the test strip loading board may be selected by those skilled in the art according to needs. For example, the length of the limiting device 120 and a mounting position of the supporting part 130 may be selected according to whether the test strip contains the water-absorbing part 230; and the number of the limiting devices 120 may be set according to the number of the sample cells 320.

As shown in FIG. 11, as one specific implementation, the detection device provided by the embodiments of the present disclosure includes:

a sample solution loading device 300, wherein the sample solution loading device 300 is provided with the sample cells 320 having the same quantity as the test strips 200; the sample cells 320 is provided with the first side wall 321, and the second side wall 322 higher than the first side wall 321. The sample cells 320 are arranged along the same circumference; the first side walls 321 are encircled into a cylinder; a bottom board 310 is arranged on the cylinder so as to form the residual sample solution containing cavity 330; and the second side walls 322 are encircled into a cylinder so as to form the outer wall of the sample solution loading device;

a test strip 200, including a capillary part 210, a color-developing part 220 and a water-absorbing part 230 arranged in sequence, wherein an identity information loading part 250 covers the surface of the water-absorbing part 230; a test strip loading board 100, wherein the upper surface of the test strip loading board 100 is a white diffuse reflection surface and is in the shape of a regular polygon; the test strip loading board 100 includes a board body 110, and test strip loading grooves 121 formed in the board body 110; and the test strip loading grooves 121 are arranged on the board body in the circumferential array surrounding the center of the circular ring area; and a signal acquisition and positioning assistance device, including a blue square identifier 144 and three green square identifiers 141, 142 and 143 arranged on the test strip loading board, wherein connecting lines of geometric centers of the identifiers 141, 142, 143 and 144 are encircled into a square area; the intersection of diagonal lines of the square area coincides with the center of the regular polygon; and each of the identifiers 141, 142, 143 and 144 is provided with two sides parallel to one side of the square area.

Effect Verification:

(1) sample solutions of different concentrations are arranged in the sample cells 320; and 6 test strips for a pesticide imidacloprid are obliquely inserted into the sample cells 320 for conducting color-developing chromatography;

(2) the test strips subjected to color developing in the step (1) are arranged in the test strip loading grooves 121 of the test strip loading board 100 and shot by a mobile phone; the shot images are uploaded to the data processing center so as to obtain a value T/C-mobile phone; and (3) the test strips subjected to color developing in the step (1) are arranged in a handheld food safety analyzer GT-710 (Beijing Qinbang Biotechnology Co., Ltd.) so as to obtain a value T/C-instrument.

Test results are shown as Table 1:

TABLE 1

| Test strip No. | Value T/C-mobile phone | Value T/C-instrument |
| --- | --- | --- |
| 1 | 0.283 | 0.223 |
| 2 | 0.182 | 0.147 |
| 3 | 0.795 | 0.674 |
| 4 | 0.707 | 0.533 |
| 5 | 0.151 | 0.126 |
| 6 | 0.095 | 0.089 |

The value T/C-mobile phone and the value T/C-instrument are subjected to linear fitting so as to obtain $R^2=0.9912$, i.e., trend variation of the two values is highly related.

It can be seen from the above test results that, when a positive sample solution is detected, the value T/C acquired by shooting the detection device in the embodiments of the present disclosure with a mobile terminal (such as a mobile phone) is higher than the acquired value T/C acquired by the instrument, this is because the two detection scenes have different light source environments, the instrument is equipped with an independent light source and the acquired image has high contrast ratio; while the ambient light shot by the mobile phone is dark and low in contrast ratio. However, it can be seen from linear fitting results of the two values that, the variation trend of the two is highly consistent, i.e., determination of the screening results of the targets is consistent when respectively independent standard curves (or standard databases) are selected.

Figure 12:
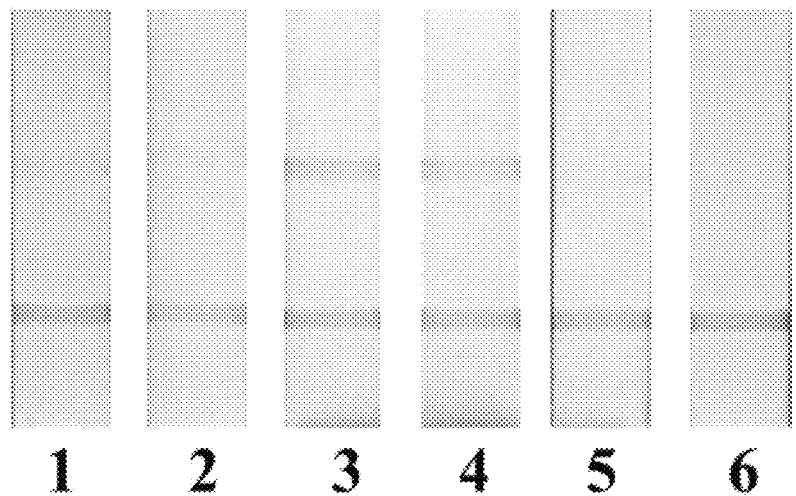
FIG. 12 shows an image of a color-developing part of the test strip obtained by shooting and uploading the image to a data processing center for segmentation in embodiments of the present disclosure.
Figure 13:
FIG. 13 shows an image of an existing rapid detection test strip shot by a mobile phone provided by embodiments of the present disclosure.

FIG. 12 shows an image of the color-developing part of the test strip obtained by shooting and uploading the image to the data processing center for segmentation; and FIG. 13 shows an image of an existing rapid detection test strip shot by a mobile phone. It can be seen from FIGS. 12 and 13 that, the color-developing part of the existing rapid detection test strip shot by the mobile phone has obvious shadow, while the segmented image shot by the mobile phone by using the detection device in the embodiments of the present disclosure has very little shadow. Due to absence of the shadow, the determination accuracy and precision of the image identification results can be greatly increased.

The above descriptions are merely specific embodiments of the present disclosure, rather than limiting the present disclosure. Various changes and modifications may be made to the present disclosure by those skilled in the art.

Modifications, equivalent replacements and improvements made in the spirit and principle of the present disclosure shall be included in the protection scope of the present disclosure.

INDUSTRIAL APPLICABILITY

In conclusion, the present disclosure provides a detection device, a sample solution loading device, a test strip loading board and a test strip. Thus, the accuracy of data acquisition can be increased; and the reliability and precision of target screening can be increased.

The invention claimed is:

1. A detection device, characterized by comprising:
a sample solution loading device comprising two or more sample cells configured to contain sample solutions;
a test strip that at least comprises an identity information loading part, a color-developing part and a capillary part;
a test strip loading board configured to radially place test strips in a circumferential array in a same circular ring area; and
a signal acquisition and positioning assistance device arranged on the test strip loading board and positioned outside a test strip arrangement area.

2. The detection device according to claim 1, characterized in that the signal acquisition and positioning assistance device comprises at least three identifiers, wherein at least one identifier can be distinguished from other identifiers of the at least three identifiers.

3. The detection device according to claim 2, characterized in that the circular ring area is divided into a first circular ring area, a second circular ring area and a third circular ring area;
when the test strips are arranged in the circumferential array, the second circular ring area is a circular ring area in which the identity information loading part and the color-developing part are positioned; the third circular ring area is a circular ring area in which the color-developing part is positioned; the first circular ring area is a circular ring area of the whole circular ring area beyond the second circular ring area;
the at least three identifiers are arranged in the second circular ring area;
or, the identifiers are close to the edge of the test strip loading board;
or, distribution of the at least three identifiers comprises circumferential array distribution surrounding the center of the circular ring.

4. The detection device according to claim 2, characterized in that the identifiers are distinguished by any one or at least two of color, shape or pattern;
and/or, the size of a side length of each identifier is more than or equal to 2 mm;
and/or, the area of each of the identifiers accounts for 0.4-5% of the area of an upper surface of the test strip loading board;
and/or, connecting lines of geometric centers of the identifiers are encircled into a square area, and the center of the square area coincides with the center of the circular ring area;
and/or, the identifiers are square identifiers; connecting lines of the centers of the square identifiers are encircled into a square area; and at least two sides of the square identifiers are parallel to the sides of the square area.

5. The detection device according to claim 4, characterized in that the identifiers are distinguished by the colors; and the colors comprise any one or a combination of at least two of blue, green and yellow;
and/or, the identifiers comprise one blue square identifier and three green square identifiers;
and/or, the identifiers comprise one green square identifier and three blue square identifiers;
and/or, the shape of the identifiers comprises any one or a combination of at least two of rectangle, triangle and pentagram.

6. The detection device according to claim 4, characterized in that the upper surface of the test strip loading board is a regular polygon; and when the test strips are arranged in a circumferential array, the test strips or extended areas of length directions of the test strips cover endpoints of the regular polygon;
and/or, when the test strips are arranged in the circumferential array, the upper surface of the test strips is lower than the upper surface of the test strip loading board; and a distance value between the upper surface of the test strips and the upper surface of the loading board is less than 1/3 of a width value of the test strips; or the upper surface of the test strip is flush with the upper surface of the test strip loading board; or the upper surface of the test strip is higher than the upper surface of the test strip loading board.

7. The detection device according to claim 6, characterized in that when the test strips are arranged in the circumferential array, the test strip loading board can at least load the identity information loading part and the color-developing part of the test strips;
and/or, a vertex, which is the farthest away from the center of the regular polygon, of each identifier on the test strip loading board is positioned on the circumference of a maximum inscribed circle of the regular polygon.

8. The detection device according to claim 6, characterized in that the upper surface of the test strip loading board is a diffuse reflection surface;
or, the upper surface of the test strip loading board is a neutral color surface.

9. The detection device according to claim 1, characterized in that the test strip loading board comprises a board body, and a test strip limiting device arranged on the board body; and the test strip limiting device is configured to limit the test strips when the test strips are arranged in the circumferential array in the same circular ring area;
and/or, the test strip loading board comprises a board body, and test strip loading grooves formed in the board body; the test strip loading grooves are arranged in a circumferential array on the board body surrounding the center of the circular ring area;
and/or, the sample solution loading device and the test strip loading board are arranged independently;
and/or, the sample solution loading device comprises at least two sample cells that can independently contain sample solutions; and each of the sample cells has the same volume;
and/or, each of the sample cells is provided with a first side wall and a second side wall that are arranged opposite to each other and have a height difference; the first side wall is the one with a lower height; the second side wall is the one with a higher height; the first side wall of each of the sample cells is integrally designed and encircled into a residual sample solution containing cavity; or the detection device further comprises a third side wall; and the first wall and the third side wall are integrally designed and encircled into the residual sample solution containing cavity;
and/or, the sample solution loading device comprises sample cells having the same quantity as the test strips; the sample cells are provided with first side walls, and second side walls higher than the first side walls; the sample cells are arranged along the same circumference; the first side walls are encircled into a cylinder; a bottom board is arranged at the bottom of the cylinder so as to form the residual sample solution containing cavity; and the second side walls are encircled into a cylinder so as to form the outer wall of the sample solution loading device;
and/or, the sample solution loading device is in detachable connection with the test strip loading board;
and/or, an embedded groove is formed in the test strip loading board; and a bulged part matched with the embedded groove is arranged at the bottom of the sample solution loading device;
and/or, the test strips further comprise a water-absorbing part;
and/or, the color-developing part is provided with a T line and a C line; a distance between the T line and the C line of the color-developing part is 5-8 mm; and a line width of the T line and the C line is 0.5-1 mm;
and/or, the signal acquisition and positioning assistance device is used for positioning each of the test strips during signal acquisition.

10. The detection device according to claim 9, characterized in that the test strip limiting device comprises any one or a combination of at least two of a limiting block, a limiting groove, a limiting baffle and a limiting slot;
and/or, the length of the test strip loading grooves is more than or equal to the sum of lengths of the identity information loading part and the color-developing part;
and/or, a depth of the test strip loading grooves is matched with a thickness of the test strip;
and/or, the depth of each of the test strip loading grooves is greater than the thickness of each test strip; and supporting parts are arranged at the bottoms of the test strip loading grooves, used for separating the lower surfaces of the test strips from the bottoms of the test strip loading grooves;
and/or, notches configured to fix the test strips are formed in the second side walls; and/or, at least the width of the bottom of the first side wall is matched with the width of the test strips;
and/or, a groove width of the test strip loading grooves is 0.1-0.2 mm wider than that of the test strip;
and/or, a shape of the end of a loading area of the identity information loading part of the test strip loading grooves is matched with the shape of the end of the identity information loading part;
and/or, a leakage channel smaller than the width of the capillary part is formed in the bottom of the sample cells; and an outlet of the leakage channel is formed above the capillary part when the test strips are arranged in the circumferential array;
and/or, the detachable connection comprises any one or a combination of at least two of buckled connection, concave-convex matched connection, threaded connection and magnetic connection;
and/or, the identity information loading part covers the upper surface of the capillary part and/or the water-absorbing part;
and/or, the signal acquisition and positioning assistance device is used for positioning the position area of the identity information loading part and the position area of the color-developing part of each test strip during signal acquisition.

11. The detection device according to claim 10, characterized in that according to the height of the supporting part, the upper surface of the color-developing part of the test strip can be elevated to be flush with the upper surface of the test strip loading board, or the upper surface of the test strip can be elevated to be higher than the upper surface of the test strip loading board;

and/or, at least two supporting parts are arranged;
and/or, the width of the notches is matched with the width of the test strips.

12. The detection device according to claim 1, characterized in that the detection device comprises:
a sample solution loading device, wherein the sample solution loading device comprises sample cells having the same quantity as the test strips; the sample cells are provided with first side walls, and second side walls higher than the first side walls; the sample cells are arranged along the same circumference; the first side walls are encircled into a cylinder; a bottom board is arranged at the bottom of the cylinder so as to form the residual sample solution containing cavity; and the second side walls are encircled into a cylinder so as to form the outer wall of the sample solution loading device;
a test strip, comprising a capillary part, a color-developing part and a water-absorbing part arranged in sequence, wherein an identity information loading part covers the upper surface of the water-absorbing part;
a test strip loading board, wherein the upper surface of the test strip loading board is a white diffuse reflection surface and is in the shape of a regular polygon; the test strip loading board comprises a board body, and test strip loading grooves formed in the board body; according to the test strip loading grooves, the upper surface of the color-developing part of the test strip is flush with the upper surface of the test strip loading board; and the test strip loading grooves are arranged on the board body in a circumferential array surrounding the center of a circular ring area;
a signal acquisition and positioning assistance device, comprising one blue square identifier and three green square identifiers arranged on the test strip loading board, wherein connecting lines of geometric centers of the square identifiers are encircled into a square area; the center of the square area coincides with the center of the circular ring area; at least two sides of the square identifiers are parallel to sides of the square area; and a vertex, which is the farthest away from the center of the circle, of the square identifier is positioned on the edge of the test strip loading board in the shape of the regular polygon.

13. A sample solution loading device used in the detection device of claim 1, characterized by comprising at least two sample cells that can independently contain sample solutions; and each of the sample cells has the same volume, wherein
the sample cells is provided with a first side wall and a second side wall that are arranged opposite to each other and have a height difference; the first side wall is the one with a lower height; and the second side wall is the one with a higher height; and
the first side wall of each of the sample cells is integrally designed and encircled into a residual sample solution containing cavity; or the sample solution loading device further comprises a third side wall; and the first wall and the third side wall are integrally designed and encircled into the residual sample solution containing cavity.

14. The sample solution loading device according to claim 13, characterized in that the notches configured to fix the test strips are formed in the second side walls;
and/or, at least the width of the bottom of the first side wall is matched with the width of the test strips;
and/or, the sample solution loading device is provided with the sample cells having the same quantity as the test strips; the sample cells are provided with the first side wall, and the second side wall higher than the first side wall; the sample cells are arranged along the same circumference; the first side walls are encircled into a cylinder; a bottom board is arranged at the bottom of the cylinder so as to form the residual sample solution containing cavity; and the second side walls are encircled into a cylinder so as to form the outer wall of the sample solution loading device;
and/or, a leakage channel is formed in the bottom of the sample cells;
and/or, the sample solution loading device is provided with connecting components in detachable connection; the connecting components comprise any one or a combination of at least two of buckles in buckled connection, grooves in concave-convex matched connection, bulges in concave-convex matched connection, internal threads in threaded connection, external threads in threaded connection, south poles in magnetic connection and north poles in magnetic connection.

15. The sample solution loading device according to claim 14, characterized in that the width of the notches is matched with the width of the test strips.

16. A test strip loading board used in the detection device of claim 1, characterized by comprising:
a board body;
a test strip limiting device that can limit an arrangement area of the test strips, wherein the arrangement area is arranged in a circumferential array in the same circular ring area in a radial shape; and
a signal acquisition and positioning assistance device arranged on the upper surface of the board body.

17. The test strip loading board according to claim 16, characterized in that the upper surface of the board body is a regular polygon;
and/or, the signal acquisition and positioning assistance device comprises at least three identifiers, wherein at least one identifier can be distinguished from other identifiers of the at least three identifiers;
and/or, the test strip limiting device is a test strip loading groove, and a length of the test strip loading groove is $\frac{1}{2}$-$\frac{5}{4}$ of the length of the test strip;
and/or, the upper surface of the board body is a white diffuse reflection surface.

18. The test strip loading board according to claim 17, characterized in that the identifiers are close to the edge of the board body;
and/or, connecting lines of geometric centers of the identifiers are encircled into a square area;
and/or, the identifiers are square identifiers; connecting lines of geometric centers of the square identifiers are encircled into a square area; the center of the square area coincides with the center of the regular polygon; and two sides of the square identifiers are parallel to sides of the square area;

and/or, the identifiers comprise one blue square identifier and three green square identifiers, or one green square identifier and three blue square identifiers;

and/or, a depth of the test strip loading groove is greater than the thickness of the test strip; and a supporting part is arranged at the bottom of the test strip loading groove, used for separating the lower surface of the test strip from the bottom of the test strip loading groove when the test strip is limited;

and/or, the edge of the test strip loading groove is matched with the edge of a to-be-limited test strip;

and/or, the quantity of the supporting parts is at least two.

\* \* \* \* \*